(12) United States Patent
Ouimette et al.

(10) Patent No.: US 10,172,354 B2
(45) Date of Patent: Jan. 8, 2019

(54) SYNERGISTIC FUNGICIDAL MIXTURES FOR FUNGAL CONTROL IN CEREALS

(71) Applicant: Dow Agrosciences LLC, Indianapolis, IN (US)

(72) Inventors: David G. Ouimette, Carmel, IN (US); J. Todd Mathieson, Brownsburg, IN (US); Gregory M. Kemmitt, Oxfordshire (GB)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/141,644

(22) Filed: Dec. 27, 2013

(65) Prior Publication Data

US 2014/0187587 A1  Jul. 3, 2014

Related U.S. Application Data

(60) Provisional application No. 61/747,094, filed on Dec. 28, 2012.

(51) Int. Cl.
*A01N 43/40* (2006.01)

(52) U.S. Cl.
CPC .................. *A01N 43/40* (2013.01)

(58) Field of Classification Search
CPC .................................................. A01N 43/30
See application file for complete search history.

(56) References Cited

U.S. PATENT DOCUMENTS

| | | |
|---|---|---|
| 4,051,173 A | 9/1977 | Schacht et al. |
| 4,588,735 A | 5/1986 | Spatz |
| 5,342,835 A | 8/1994 | Pepin et al. |
| 5,401,871 A | 3/1995 | Feldmann-Krane et al. |
| 5,475,132 A | 12/1995 | Pepin et al. |
| 5,563,165 A | 10/1996 | Talley |
| 5,760,068 A | 6/1998 | Talley |
| 5,852,042 A | 12/1998 | Jakobi et al. |
| 6,355,660 B1 | 3/2002 | Ricks |
| 6,410,572 B1 | 6/2002 | Schelberger et al. |
| 6,436,421 B1 | 8/2002 | Schindler et al. |
| 6,521,622 B1 | 2/2003 | Ricks |
| 6,706,740 B2 | 3/2004 | Ricks |
| 6,861,390 B2 | 3/2005 | Meyer |
| 6,916,932 B2 | 7/2005 | Meyer et al. |
| 6,927,225 B2 | 8/2005 | Ricks |
| 6,953,807 B2 | 10/2005 | Hutin |
| 7,034,035 B2 | 4/2006 | Ricks |
| 7,183,278 B1 | 2/2007 | Imamura |
| 7,250,389 B1 | 7/2007 | Sakanaka |
| RE39,991 E | 1/2008 | Ricks et al. |
| 7,442,672 B2 | 10/2008 | Muller et al. |
| 8,465,562 B2 | 6/2013 | Chen |
| 8,470,840 B2 | 6/2013 | Klittich et al. |
| 8,476,193 B2 | 7/2013 | Keeney et al. |
| 8,580,959 B2 | 11/2013 | Devasthale et al. |
| 8,604,215 B2 | 12/2013 | Phiasivongsa et al. |
| 8,785,479 B2 | 7/2014 | Meyer |
| 8,835,462 B2 | 9/2014 | Meyer |
| 8,883,811 B2 | 11/2014 | Owen |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,156,816 B2 | 10/2015 | Ito et al. |
| 9,185,911 B2 | 11/2015 | Inami et al. |
| 9,198,419 B2 | 12/2015 | Owen et al. |
| 9,247,741 B2 | 2/2016 | DeLorbe |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,549,555 B2 | 1/2017 | DeLorbe et al. |
| 9,629,365 B2 | 4/2017 | Li et al. |
| 9,700,047 B2 | 7/2017 | Lu |
| 9,750,248 B2 | 9/2017 | Ouimette et al. |
| 9,840,475 B2 | 12/2017 | Lorsbach |
| 9,955,690 B2 | 5/2018 | Owen |
| 2002/0119979 A1 | 8/2002 | Degenhardt et al. |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2003/0022903 A1 | 1/2003 | Ricks |
| 2004/0034025 A1 | 2/2004 | Ricks |
| 2004/0048864 A1 | 3/2004 | Ricks |
| 2004/0171838 A1 | 9/2004 | Owen |
| 2004/0186296 A1 | 9/2004 | Nyaz |
| 2004/0192924 A1 | 9/2004 | Meyer |
| 2005/0239873 A1 | 10/2005 | Hockenbery |
| 2006/0040995 A1 | 2/2006 | Bacque |
| 2006/0167281 A1 | 7/2006 | Meijer |
| 2007/0010401 A1 | 1/2007 | Noon |
| 2007/0060579 A1 | 3/2007 | Wachendorff-Neumann |
| 2007/0066629 A1 | 3/2007 | Tormo I Blasco |
| 2007/0087937 A1 | 4/2007 | Leatherman |
| 2008/0070985 A1 | 3/2008 | Derrer |
| 2008/0293798 A1 | 11/2008 | Dietz |
| 2008/0318785 A1 | 12/2008 | Koltzenburg |
| 2009/0203770 A1 | 8/2009 | Hockenberry |
| 2009/0306142 A1 | 12/2009 | Carson |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Gisi, U. The American Phytopathological Society, vol. 86, No. 11, 1996, p. 1273.*

(Continued)

Primary Examiner — Sahar Javanmard
(74) Attorney, Agent, or Firm — Faegre Baker Daniels LLP

(57) ABSTRACT

A fungicidal composition containing a fungicidally effective amount of (a) the compound of Formula I, (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate, and (b) fluxapyroxad, provides synergistic control of selected fungi.

14 Claims, No Drawings

(56) References Cited

U.S. PATENT DOCUMENTS

| | | | |
|---|---|---|---|
| 2010/0016163 | A1 | 1/2010 | Keiper et al. |
| 2011/0034493 | A1 | 2/2011 | Boebel |
| 2011/0053891 | A1 | 3/2011 | Boebel et al. |
| 2011/0053966 | A1* | 3/2011 | Klittich et al. ............... 514/274 |
| 2011/0070278 | A1 | 3/2011 | Lopez |
| 2011/0082039 | A1 | 4/2011 | Keeney |
| 2011/0082160 | A1 | 4/2011 | Owen |
| 2011/0082162 | A1 | 4/2011 | Lorsbach et al. |
| 2011/0306644 | A1 | 12/2011 | Hoekstra |
| 2012/0035054 | A1 | 2/2012 | Ehr |
| 2012/0245031 | A1 | 9/2012 | Gewehr et al. |
| 2013/0090298 | A1 | 4/2013 | Lee et al. |
| 2013/0296371 | A1 | 11/2013 | Meyer |
| 2013/0296372 | A1 | 11/2013 | Owen et al. |
| 2013/0296373 | A1 | 11/2013 | Meyer |
| 2013/0296375 | A1 | 11/2013 | Meyer et al. |
| 2014/0051678 | A1 | 2/2014 | Clement-Schatlo et al. |
| 2014/0128411 | A1* | 5/2014 | Ogawa et al. ........... 514/259.31 |
| 2014/0187587 | A1 | 7/2014 | Ouimette et al. |
| 2014/0187588 | A1 | 7/2014 | Lalonde |
| 2014/0275171 | A1 | 9/2014 | Meyer |
| 2014/0357713 | A1 | 12/2014 | Damaj et al. |
| 2015/0065529 | A1 | 3/2015 | Owen |
| 2015/0289508 | A1 | 10/2015 | Meyer |
| 2015/0322051 | A1 | 11/2015 | Lu et al. |

FOREIGN PATENT DOCUMENTS

| | | | |
|---|---|---|---|
| CN | 102638989 | | 8/2012 |
| EP | 1054011 | | 11/2000 |
| EP | 1516874 | | 3/2005 |
| FR | 2649699 | | 1/1991 |
| JP | 19940026884 | | 9/1995 |
| JP | 1998053583 | | 2/1998 |
| JP | H10-045747 | | 2/1998 |
| WO | 1996010016 | | 4/1996 |
| WO | 199637472 | | 11/1996 |
| WO | 1997019908 | | 6/1997 |
| WO | 199741103 | | 11/1997 |
| WO | 1998018751 | | 5/1998 |
| WO | 1999011127 | | 3/1999 |
| WO | 2000076979 | | 12/2000 |
| WO | 2001/14339 | | 3/2001 |
| WO | 2001014365 | | 3/2001 |
| WO | 03011857 | | 2/2003 |
| WO | 03035617 | | 5/2003 |
| WO | 2005121069 | | 12/2005 |
| WO | 2007017416 | | 2/2007 |
| WO | 2008079387 | | 7/2008 |
| WO | 2009040397 | | 9/2008 |
| WO | 2011028657 | | 3/2011 |
| WO | 2011044213 | | 4/2011 |
| WO | WO 2011043876 | * 4/2011 | ............ A61J 31/505 |
| WO | 2011069893 | | 6/2011 |
| WO | 2012016972 | | 2/2012 |
| WO | 2012016989 | | 2/2012 |
| WO | 2012/070015 | | 5/2012 |
| WO | 2013110002 | | 7/2013 |
| WO | 2013116251 | | 8/2013 |
| WO | 2012020777 | | 2/2014 |
| WO | 2014105817 | | 7/2014 |
| WO | 2014105844 | | 7/2014 |
| WO | 2015100181 | | 7/2015 |
| WO | 2015100182 | | 7/2015 |
| WO | 2015103161 | | 7/2015 |
| WO | 2016007525 | | 1/2016 |

OTHER PUBLICATIONS

Kissling, Crop Protection pipeline value jumps to € 2.4 billion. BASF. Mar. 11, 2010, pp. 1-4, [retrieved on Feb. 4, 2014]. Retrieved from the Internet: <URL: http://www.agro.basf.com/agr/AP-Internet/en/content/news_room/news/basf-corp-protection-pipaline-value>.

BASF new fingicide Xemium got full approval in EU. AgroNews. Jul. 18, 2012 [retrieved on 1-20 Feb. 4, 2014). Retrieved from the Internet: <URL: http://news.agropages.com/News/NewsDetail--7386.html>.

Copenheaver, B.R., International Search Report for PCT/US2013/077537, dated Apr. 16, 2014, pp. 1-3. ISA/US.

Copenheaver, B.R., Written Opinion for PCT/US2013/077537, dated Apr. 2, 2014, pp. 1-6, ISA/US.

Anonymous, Synergistic Fungicidal Composition of Heterocyclic Aromatic Amides and Trizaoles, IP.com, Electronic Publication, 2004, 11 pages.

Anonymous, Synergistic Fungicidal Composition of Heterocyclic Aromatic Amides and Triazoles, IP.com Journal, IP.com Inc., West Henrietta, NY, US, Dates Jul. 2004, 10 pages.

K. Tani, et al, Journal of Antibiotics, vol. 55, No. 3, Mar. 2002, pp. 315-321.

Z. Hu, et al, Synthesis of Novel Analogues of Antimycin A3, Tetrahedron Letters 49 (2008) pp. 5192-5195.

Y. Usuki, et al, Journal of Antibiotics, vol. 55, No. 6, Jun. 2002, pp. 607-610.

Huang, et al., Synergistic Interactions between Chitinase ChiCW and Fungicides Against Plant Fungal Pathogens, J. Microbiol. Biotechnol., 2008, 18(4) 784-787.

Backman, P., Fungicide Formulation: Relationship to Biological Activity, 1978, 16, 211-237.

Latin, et al, Re-Examining Fungicide Synergism for Dollar Spot Control, GCM, 2008, 84-87.

O'Sullivan, et al., Fungicide Resistance—an Increasing Problem, Proceedings of National Tillage Conference 2007, Published by Crop Research Centre Oak Park Carlow, date Jan. 31, 2007, 14 pages.

Extended European Search Report for European Patent Application 13867094.8, dated Jun. 24, 2016, 6 pages.

Search report for Chinese Patent Application 201380068403.3 and English translation, dated May 25, 2016, 4 pages.

Koyanagi et al., "Bioisoterism, etc.," Synthesis and Chemistry of Agrochemicals IV; Baker, D. et al., 1995, 15-24.

Masashi Ueki et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-634.

Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.

Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.

Cantacuzene, D., "Optimization of the papain catalyzed esterification of amino acids by alcohols and diols," Tetrahedron, vol. 45, Issue 3 (1989), pp. 741-748.

Bolton, Md et al., Wheat leaf rust caused by Puccinia triticina. Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf; p. 564, col. 1, paragraph 4.

M. Davari, et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 845-855, Abstract Only.

FRAC Code List: Fungicides Sorted by Mode of Action (including FRAC Code numbering), Dec. 2008, pp. 1-10.

"Fungicidal Mixtures", IP.com Prior Art Database Technical Disclosure, (Jul. 5, 2005), pp. 1-10, XP055073888, DOI: http://ip.com/pdf/ipcompad/IPCOM000126160D.pdf.

The Merck Index, Twelfth Edition, S. Budavari, Ed., Merck and Co., Inc., Whitehouse Station, NJ, 1996, pp. 361, 615, 1332, 1333.

(56) References Cited

OTHER PUBLICATIONS

Parker, J.E., et al., "Mechanism of Binding of Prothioconazole to Mycosphaerella graminicola CYP51 Differs from That of Other Azole Antifungals," Applied and Environmental Microbiology, Feb. 2011, pp. 1460-1465.
Science for a Better Life, Bayer Cropscience, Jun. 2008, 22 pages.
"Sulfonate" (http://www.hichem.com/product/showproduct.php?id=334639), Mar. 28, 2013, p. 1-4.
Webster's New World Dictionary, 2nd college edition, The World Publishing Co., New York, p. 1127 (1972).
Wilson, C.L. et al. "Fruit Volatiles Inhibitory to Monilinia Fruiticola and Botrytis cinerea," 1987, Plant Disease 71: 316-319.
Guseynov et al: "Study of the reaction of aminoacetic acid with dihydric alcohols and production of epoxy esters" Chemical Problems, 2009 (1), pp. 188-190. English Machine Translation attached.
Goellner et al. "Phakopsora pachyrhizi, the causal agent of Asian soybean rust" Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).
Patani et al. "Biosterism: A rational approach in drug design." Chemical Reviews, vol. 96, No. 8, pp. 3147-3176 (1996).
Kendall S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total sythesis of the antifungal dilactones UK-2A and UK-3a: The determination of their relative and absolute configurations, analog synthesis and antifungal activities". Tetrahedron, vol. 54, pp. 12745-12774 (1998).
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012). (Submitted in 3 parts due to size limitations).
Lippard, S. "Chemical Synthesis: The Art of Chemistry". Nature, vol. 416, p. 587 (2002).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Ueki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
Stephenson, G., et al. "Glossary of terms relating to pesticides". Pure and Applied Chemistry, vol. 78, No. 11, pp. 2075-2154, International Union of Pure and Applied Chemistry (2006).
Chitwood, D. "Nematicides". Encyclopedia of Agrochemicals (3), pp. 1104-1115, John Wiley & Sons, New York, NY, http://naldc.nal.usda.gov/download/43874/PDF (2003).

International Searching Authority, International Search Report for PCT/US14/058070, dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US1567111 dated Mar. 11, 2016, 11 pages.
International Searching Authority, International Search Report and Written Opinion for PCT/US1567113 dated Mar. 11, 2016, 10 pages.
International Searching Authority, International Search Report and Written Opinion for PCT/US1567116 dated Mar. 7, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.
International Searching Authority, International Search Report and Written Opinion for PCT/US1567201 dated Mar. 11, 2016, 8 pages.
International Searching Authority, International Search Report and Written Opinion for PCT/US1567204 dated Mar. 7, 2016, 10 pages.
International Searching Authority, International Search Report and Written Opinion for PCT/US1567206 dated Mar. 7, 2016, 8 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2014071692 dated Apr. 20, 2015, 6 pages.
International Searching Authority, International Search Report and Written Opinion for PCT/US2015/067115, dated Mar. 11, 2016, 6 pages.
International Searching Authority, International Search Report and Written Opinion for PCT/US2014071695 dated Apr. 17, 2015, 9 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.

(56) References Cited

OTHER PUBLICATIONS

International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report and Written Opinion for PCT/US2013077537, dated Apr. 16, 2014, 11 pages.
Database Chemabs Online, Chemical Abstracts Service, Columbus Ohio, US: accession No. CA63:16300d XP002164206. (Cited in International Search Report for PCT/US2000/021523).
International Searching Authority, International Search Report for PCT/US2000/021523 dated Jul. 7, 2001, 7 pages.

\* cited by examiner

SYNERGISTIC FUNGICIDAL MIXTURES FOR FUNGAL CONTROL IN CEREALS

CROSS REFERENCE TO RELATED APPLICATIONS

This application claims the benefit of U.S. Provisional Patent Application Ser. No. 61/747,094 filed Dec. 28, 2012, which is expressly incorporated by reference herein.

FIELD

This disclosure concerns a synergistic fungicidal composition containing (a) the compound of Formula I and (b) fluxapyroxad.

BACKGROUND

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value of the crop. In most situations, the increase in value of the crop is worth at least three times the cost of the use of the fungicide.

However, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less.

Synergism occurs when the activity of two, or more, compounds exceeds the activities of the compounds when used alone.

SUMMARY

One object of this disclosure is to provide synergistic compositions comprising fungicidal compounds. Another object of this disclosure is to provide processes that use these synergistic compositions. The synergistic compositions are capable of preventing or curing, or both, diseases caused by fungi of the class Ascomycetes. In addition, the synergistic compositions have improved efficacy against the Ascomycete pathogens, including leaf blotch of wheat. In accordance with this disclosure, synergistic compositions are provided along with methods for their use.

Some embodiments include a synergistic fungicidal mixture comprising a fungicidally effective amount of the compound of Formula I and fluxapyroxad.

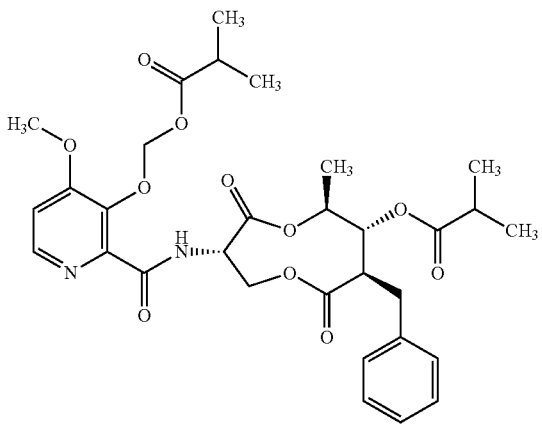

(I)

Some embodiments include a mixture of the compound of Formula I and fluxapyroxad in which the weight ratios of the compound of Formula I to fluxapyroxad is from about 1:1 to about 16:1. In some more particular embodiments, the weight ratio is from about 1:2 to about 16:1, from about 1:4 to about 16:1, or from about 1:8 to 16:1. In other more particular embodiments, the weight ratio is from about 1:1 to about 8:1, from about 1:1 to about 4:1, or about 1:1 to about 1:2.

Some embodiments include a mixture of the compound of Formula I and fluxapyroxad in which the weight ratios of the compound of Formula I to fluxapyroxad includes ratios selected from the group of ratios consisting of: about 1:1, about 1:2, about 1:3, about 1:4, about 1:5, about 1:6, about 1:7, about 1:8, about 1:9, about 1:10, about 1:11, about 1:12, about 1:13, about 1:14, about 1:16, about 2:1, about 3:1, about 4:1, about 5:1, about 6:1, about 7:1, about 8:1, about 9:1, about 10:1, about 11:1, about 12:1, about 13:1, about 14:1, and about 16:1, or within any range defined between any two of the foregoing values.

Some embodiments include a mixture wherein the ratio of the compound of Formula I to fluxapyroxad is about 1 to about 1. Some embodiments include a mixture wherein the ratio of the compound of Formula I to fluxapyroxad is about 1 to about 2. Some embodiments include a mixture wherein the ratio of the compound of Formula I to fluxapyroxad is about 1 to about 3. Some embodiments include a mixture wherein the ratio of the compound of Formula I to fluxapyroxad is about 1 to about 4. Some embodiments include a mixture wherein the ratio of the compound of Formula I to fluxapyroxad is about 1 to about 5. Some embodiments include a mixture wherein the ratio of the compound of Formula I to fluxapyroxad is about 1 to about 6. Some embodiments include a mixture wherein the ratio of the compound of Formula I to fluxapyroxad is about 1 to about 7. Some embodiments include a mixture wherein the ratio of the compound of Formula I to fluxapyroxad is about 1 to about 8. Some embodiments include a mixture wherein the ratio of the compound of Formula I to fluxapyroxad is about 1 to about 9. Some embodiments include a mixture wherein the ratio of the compound of Formula I to fluxapyroxad is about 1 to about 10. Some embodiments include a mixture wherein the ratio of the compound of Formula I to fluxapyroxad is about 1 to about 11. Some embodiments include a mixture wherein the ratio of the compound of Formula I to fluxapyroxad is about 1 to about 12. Some embodiments include a mixture wherein the ratio of the compound of Formula I to fluxapyroxad is about 1 to about 13. Some embodiments include a mixture wherein the ratio of the compound of Formula I to fluxapyroxad is about 1 to about 14. Some embodiments include a mixture wherein the ratio of the compound of Formula I to fluxapyroxad is about 1 to about 16. Still other embodiments include a fungicidal composition comprising a fungicidally effective amount of the fungicidal mixture and an agriculturally acceptable adjuvant or carrier.

Yet other embodiments include methods of treating a plant, comprising the step of: applying a fungicidally effective amount of a mixture that includes the compound of Formula 1 and fluxapyroxad to a surface selected from at least one surface selected from the group of surfaces consisting of: at least one portion of a plant, soil adjacent to a plant, soil in contact with a plant, seeds, and equipment used in contact with a plant or a surface adjacent to a plant. In some embodiments, the fungicidally effective amount of the mixture is applied in the range of about 30 grams/hectare (g/ha) to about 200 g/ha of fluxapyroxad and about 35 g/ha to about 300 g/ha of the compound of Formula 1.

DETAILED DESCRIPTION

The present disclosure concerns a synergistic fungicidal mixture comprising a fungicidally effective amount of (a) the compound of Formula I, (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate, and (b) fluxapyroxad, 3-(difluoromethyl)-1-methyl-N-(3',4',5'-trifluorobiphenyl-2-yl)pyrazole-4-carboxamide.

The compound of Formula I is described in U.S. Pat. No. 6,861,390 (which is incorporated herein by reference in its entirety).

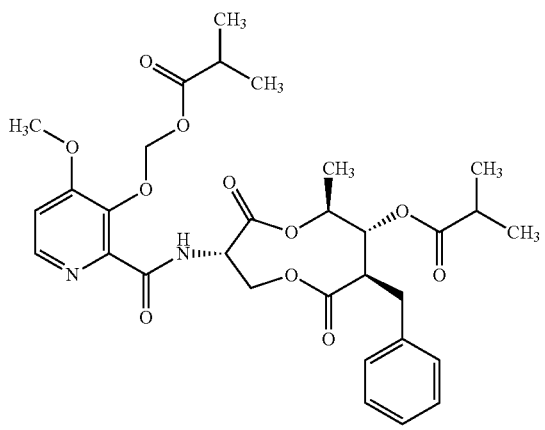

Fluxapyroxad is described in *The e-Pesticide Manual*, Version 5.2, 2011. The structure of fluxapyroxad is as follows:

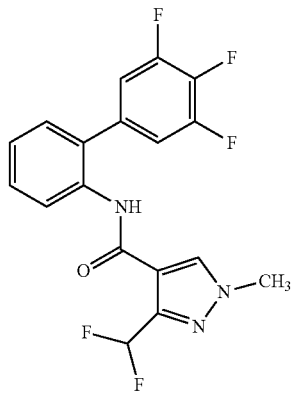 [SMILES: Cn1cc(C(=O)Nc2ccccc2-c2cc(F)c(F)c(F)c2)c(C(F)F)n1]

In the composition described herein, the weight ratios of the compound of Formula I to fluxapyroxad at which the fungicidal effect is synergistic includes ratios in the ranges of about 1:1, about 1:2, about 1:3, about 1:4, about 1:5, about 1:6, about 1:7, about 1:8, about 1:9, about 1:10, about 1:11, about 1:12, about 1:13, about 1:14, about 1:16, about 2:1, about 3:1, about 4:1, about 5:1, about 6:1, about 7:1, about 8:1, about 9:1, about 10:1, about 11:1, about 12:1, about 13:1, about 14:1, and about 16:1. Unless clearly noted or clearly implied otherwise, the term "about", as used herein, refers to a range of plus or minus 10%, e.g., about 1 includes the range of values from 0.9 to 1.1.

The rate at which the synergistic composition is applied will depend upon the particular type of fungus to be controlled, the degree of control required and the timing and method of application. In general, the composition of the disclosure can be applied at an application rate of between about 50 grams per hectare (g/ha) and about 1500 g/ha based on the total amount of active ingredients in the composition. In other embodiments, the composition of the disclosure can be applied at an application rate of between about 65 grams per hectare (g/ha) and about 500 g/ha based on the total amount of active ingredients in the composition. Fluxapyroxad is applied at a rate between about 30 g/ha and about 200 g/ha and the compound of Formula I is applied at a rate between about 35 g/ha and about 300 g/ha.

The components of the synergistic mixture of the present disclosure can be applied either separately or as part of a multipart fungicidal system. The synergistic mixture of the present disclosure can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, N-3, 5-dichlorophenyl-succinimide, N-3-nitrophenylitaconimide, 2-(thiocyanatomethylthio)-benzothiazole, (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S- methyl, acypetacs, acypetacs-copper, acypetacs-zinc, albendazole, aldimorph, allicin, allyl alcohol, ametoctradin, amisulbrom, amobam, *Ampelomyces quisqualis*, ampropylfos, anilazine, antimycin, asomate, aureofungin, azaconazole, azithiram, azoxystrobin, *Bacillus subtilis, Bacillus subtilis* strain QST713, barium polysulfide, Bayer 32394, benalaxyl, benalaxyl-M, benquinox, benodanil, benomyl, bentaluron, benthiavalicarb, benthiavalicarb-isopropyl, benthiazole, benzamacril, benzamacril-isobutyl, benzamorf, benzohydroxamic acid, benzovindiflupyr, benzylaminobenzene-sulfonate (BABS) salt, berberine, berberine chloride, bethoxazin, bicarbonates, bifujunzhi, binapacryl, biphenyl, bismerthiazol, bis(methylmercury) sulfate, bis(tributyltin) oxide, bitertanol, bithionol, bixafen, blasticidin-S, borax, Bordeaux mixture, boscalid, bromothalonil, bromuconazole, bupirimate, Burgundy mixture, buthiobate, butylamine, cadmium calcium copper zinc chromate sulfate, calcium polysulfide, *Candida oleophila*, captafol, captan, carbamorph, carbendazim, carbendazim benzenesulfonate, carbendazim sulfite, carboxin, carpropamid, carvacrol, carvone, CECA, Cheshunt mixture, chinomethionat, chitosan, chlazafenone, chlobenthiazone, chloraniformethan, chloranil, chlorfenazole, chlorodinitronaphthalenes, chlorquinox, chloroneb, chloropicrin, chlorothalonil, chlozolinate, climbazole, clotrimazole, *Coniothyrium minitans*, copper acetate, copper bis(3-phenylsalicylate), copper carbonate, basic, copper hydroxide, copper naphthenate, copper octanoate, copper oleate, copper oxychloride, copper silicate, copper sulfate, copper sulfate (tribasic), copper zinc chromate, coumoxystrobin, cresol, cufraneb, cupric hydrazinium sulfate, cuprobam, cuprous oxide, cyazofamid, cyclafuramid, cycloheximide, cyflufenamid, cymoxanil, cypendazole, cyproconazole, cyprodinil, cyprofuram, dazomet, dazomet-sodium, DBCP, debacarb, decafentin, dehydroacetic acid, diammonium ethylenebis-(dithiocarbamate), dichlofluanid, dichlone, dichloran, dichlorophen, dichlozoline, diclobutrazol, diclocymet, diclomezine, diclomezine-sodium, diethofencarb, diethyl pyrocarbonate, difenoconazole, difenzoquat ion, diflumetorim, dimetachlone, dimethirimol, dimethomorph, dimoxystrobin, dingjunezuo, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, dithioether, DNOC, DNOC-ammonium, DNOC-potassium, DNOC-sodium, dodemorph, dodemorph acetate, dodicin, dodicin hydrochloride, dodicin-sodium, dodine, dodine free base, drazoxolon, EBP, edifenphos, enestrobin, enestroburin, enoxastrobin, epoxiconazole, ESBP, etaconazole, etem, ethaboxam, ethirim, ethirimol, ethoxyquin, etirimol, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenaminstrobin, fenapanil, fenarimol, fenbuconazole, fenfuram, fenhexamid, fenitropan, fenjuntong, fenoxanil, fenpiclonil, fenpropidin, fenpropimorph, fenpyrazamine, fentin, fentin acetate, fentin chloride, fentin hydroxide, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, fluthiacet-methyl, flutianil, flutolanil, flutriafol, folpet, formaldehyde, fosetyl, fosetyl-aluminium, fuberidazole, furalaxyl, furametpyr, furcarbanil, furconazole, furconazole-cis, furfural, furmecyclox, furophanate, *Fusarium oxysporum, Gliocladium* spp., glyodine, griseofulvin, guazatine, guazatine acetates, GY-81, halacrinate, Hercules 3944, hexachlorobenzene, hexachlorobutadiene, hexachlorophene, hexaconazole, hexylthiofos, huanjunzuo, hydrargaphen, hymexazol, ICIA0858, imazalil, imazalil nitrate, imazalil sulfate, imibenconazole, iminoctadine, iminoctadine triacetate, iminoctadine tris(albesilate), inezin, iodocarb, iodomethane, ipconazole, ipfenpyrazolone, iprobenfos, iprodione, iprovalicarb, isopamphos, isoprothiolane, isopyrazam, isotianil, isovaledione, jiaxiangjunzhi, kasugamycin, kasugamycin hydrochloride hydrate, kejunlin, kresoxim-methyl, laminarin, lvdingjunzhi, mancopper, mancozeb, mandipropamid, maneb, mebenil, mecarbinzid, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl iodide, methyl isothiocyanate, methylmercury benzoate, methylmercury dicyandiamide, methylmercury pentachlorophenoxide, metiram, metominostrobin, metrafenone, metsulfovax, mildiomycin, milneb, moroxydine, moroxydine hydrochloride, mucochloric anhydride, myclobutanil, myclozolin, N-ethylmercurio-4-toluenesulfonanilide, N-(ethylmercury)-p-toluenesulphonanilide, nabam, natamycin, nickel bis(dimethyldithiocarbamate), nitrostyrene, nitrothal-isopropyl, nuarimol, OCH, octhilinone, ofurace, oleic acid (fatty acids), orysastrobin, osthol, oxadixyl, oxathiapiprolin, oxine-copper, oxpoconazole fumarate, oxycarboxin, parinol, pefurazoate, penconazole, pencycuron, penflufen, pentachlorophenol, pentachlorophenyl laurate, penthiopyrad, phenamacril, phenylmercuriurea, phenylmercury acetate, phenylmercury chloride, phenylmercury derivative of pyrocatechol, phenylmercury dimethyldithiocarbamate, phenylmercury nitrate, phenylmercury salicylate, *Phlebiopsis gigantea*, phosdiphen, phosphonic acid, phthalide, picoxystrobin, piperalin, polycarbamate, polyoxin B, polyoxins, polyoxorim, polyoxorim-zinc, potassium azide, potassium bicarbonate, potassium hydroxyquinoline sulfate, potassium polysulfide, potassium thiocyanate, probenazole, prochloraz, prochloraz-manganese, procymidone, propamidine, propamidine dihydrochloride, propamocarb, propamocarb hydrochloride, propiconazole, propineb, proquinazid, prothiocarb, prothiocarb hydrochloride, prothioconazole, pyracarbolid, pyraclostrobin, pyrametostrobin, pyraoxystrobin, pyrazophos, pyribencarb, pyributicarb, pyridinitril, pyrifenox, pyrimethanil, pyriofenone, pyrisoxazole, pyroquilon, pyroxychlor, pyroxyfur, quinacetol, quinacetol sulfate, quinazamid, quinoclamine, quinconazole, quinoxyfen, quintozene, rabenzazole, *Reynoutria sachalinensis* extract, saisentong, salicylanilide, santonin, sedaxane, silthiofam, simeconazole, sodium 2-phenylphenoxide, sodium azide, sodium bicarbonate, sodium orthophenylphenoxide, sodium pentachlorophenoxide, sodium polysulfide, spiroxamine, *Streptomyces griseoviridis*, streptomycin, streptomycin sesquisulfate, SSF-109, sulfur, sultropen, SYP-Z048, tar oils, tebuconazole, tebufloquin, tecloftalam, tecnazene, tecoram, tetraconazole, thiabendazole, thiadifluor, thicyofen, thifluzamide, thiochlorfenphim, thiodiazole-copper, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, triclopyricarb, *Trichoderma* spp., tricyclazole, tridemorph, trifloxystrobin, triflumizole, triforine, triticonazole, uniconazole, uniconazole-P, urbacid, validamycin, valifenalate, valiphenal, vangard, vinclozolin, xiwojunan, zarilamid, zineb, zinc naphthenate, zinc thiazole, ziram, and zoxamide, and any combinations thereof.

The compositions described herein are preferably applied in the form of a formulation comprising a composition of (a)

the compound of Formula I and (b) fluxapyroxad, together with a phytologically acceptable carrier.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present disclosure contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water dispersible granules, comprise an intimate mixture of the synergistic composition, a carrier and agriculturally acceptable surfactants. The concentration of the synergistic composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 10% to about 50% by weight, in a suitable liquid, based on the total weight of the emulsifiable concentrate formulation. The components of the synergistic compositions, jointly or separately, are dissolved in a carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil soluble salts or sulfated polyglycol ethers and appropriate salts of phosphated polyglycol ether.

Representative organic liquids which can be employed in preparing the emulsifiable concentrates of the present disclosure are the aromatic liquids such as xylene, propyl benzene fractions, or mixed naphthalene fractions, mineral oils, substituted aromatic organic liquids such as dioctyl phthalate, kerosene, dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as a granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from 0.01 percent to 1.0 percent volume/volume (v/v) based on a spray-volume of water, preferably 0.05 to 0.5 percent. Suitable adjuvant surfactants include ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present disclosure in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

The present disclosure includes within its scope methods for the control or prevention of fungal attack. These methods comprise applying to the fungus or the area adjacent to the the fungus, or to a plant or area adjacent to a plant in which the infestation is to be prevented (for example applying to wheat or barley plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition is applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition is applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect particularly for agricultural use. The synergistic composition is particularly effective for use with agricultural crops and horticultural plants, or with wood, paint, leather or carpet backing.

In particular, the synergistic composition is effective in controlling a variety of undesirable fungi that infect useful plant crops. The synergistic composition can be used against a variety of Ascomycete and Basidiomycete fungi, including for example the following representative fungi species: wheat brown rust (*Puccinia recondita*; Bayer code PUCCRT); stripe rust of wheat (*Puccinia striiformis*; Bayer code PUCCST); leaf blotch of wheat (*Mycosphaerella graminicola*; anamorph: *Septoria tritici*; Bayer code SEPTTR); glume blotch of wheat (*Leptosphaeria nodorum*; Bayer code LEPTNO; anamorph: *Stagonospora nodorum*) and black sigatoka disease of banana (*Mycosphaerella fijiensis*; BAYER code MYCOFI). It will be understood by those in the art that the efficacy of the synergistic compositions for one or more of the foregoing fungi establishes the general utility of the synergistic compositions as fungicides.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease inhibiting and phytologically acceptable amount. The term "disease inhibiting and phytologically acceptable amount" refers to an amount of the synergistic composition that kills or inhibits the plant disease for which control is desired, but is not significantly toxic to the plant. The exact concentration of synergistic composition required varies with the fungal disease to be controlled, the type of formulation employed, the method of application, the particular plant species, climate conditions, and the like.

The present compositions can be applied to fungi or the area adjacent to the fungus, or a plant or area adjacent to the plant, by the use of conventional ground sprayers, granule applicators, and by other conventional means known to those skilled in the art.

The following examples are provided to further illustrate the disclosure. They are not meant to be construed as limiting the disclosure.

EXAMPLES

Representative synergistic interactions, including application rates employed and resulting disease control of wheat brown rust and wheat leaf blotch is presented in Table 1.

For the mixture studies with the compound of Formula I: Treatments consisted of fungicides, including the compound of Formula I and fluxapyroxad. Technical grades of materials were dissolved in acetone to make stock solutions, which were then used to perform 4-fold dilutions in acetone for each individual fungicide component or for the two-way mixture. Desired fungicide rates were obtained after mixing dilutions with 9 volumes of water containing 110 parts per million (ppm) Triton X-100. The fungicide solutions (20 milliliters (mL)) were applied to 12 pots of plants using an automated booth sprayer, which utilized two 6218-1/4 JAUPM spray nozzles operating at 20 pounds per square inch (psi) set at opposing angles to cover both leaf surfaces. All sprayed plants were allowed to air dry prior to further handling. Control plants were sprayed in the same manner with a solvent blank.

Evaluation of Curative and Protectant Activity of Fungicide Mixtures vs. Leaf Blotch of Wheat (*Mycosphaerella graminicola*; Anamorph: *Septoria tritici*; Bayer Code: SEPTTR).

Wheat plants (variety Yuma) were grown from seed in a greenhouse in plastic pots with a surface area of 27.5 square centimeters ($cm^2$) containing 50% mineral soil/50% soilless Metro mix, with 8-12 seedlings per pot. The plants were utilized for testing when the first leaf was fully emerged, which typically occurred 7-8 days after planting. Test plants were inoculated with an aqueous spore suspension of *Septoria tritici* either (a) 3 days prior to fungicide treatments (3-day curative test, 3DC) or (b) 1 day after fungicide treatments (1-day protectant test, 1DP). After inoculation the plants were placed in a dew room from 1-3 days to allow for infection to occur. The plants were then placed in the greenhouse for symptom development to occur, which in the case of SEPTTR typically required 25-30 days.

Evaluation of Curative Activity of Fungicide Mixtures vs. Wheat Brown Rust (*Puccinia recondita*; Bayer Code: PUC-CRT).

Yuma wheat seedlings were grown as described above and inoculated with an aqueous spore suspension of *Puccinia recondita* 3 days prior to fungicide treatment (3DC). After inoculation, plants were placed in a dew room for 1 day to allow for infection to occur. The plants were then placed in the greenhouse for symptom development to occur, which in the case of PUCCRT typically required 7-10 days.

When disease severity reached 50-100% on the control plants, infection levels were assessed on treated plants visually and scored on a scale of 0 to 100 percent. The percentage of disease control was then calculated using the ratio of disease on treated plants relative to control plants.

The Colby equation was used to determine the fungicidal effects expected from the mixtures. (See Colby, S. R. Calculation of the synergistic and antagonistic response of herbicide combinations. *Weeds* 1967, 15, 20-22.)

The following equation was used to calculate the expected activity of mixtures containing two active ingredients, A and B:

$$\text{Expected} = A + B - (A \times B / 100)$$

A=observed efficacy of active component A at the same concentration as used in the mixture;
B=observed efficacy of active component B at the same concentration as used in the mixture.

The treatments that were evaluated, the application rates employed, the pathogens evaluated, and resulting diseases in both the treated and the control plants are presented in Table 1.

TABLE 1

Synergistic interactions of compound I and fluxapyroxad in 1-day protectant (1DP) *Septoria tritici* (SEPTTR) and 3-day curative *Puccinia recondita* (PUCCRT) tests.

| Application Rate | | SEPTTR 1DP | | PUCCRT 3DC | |
|---|---|---|---|---|---|
| (ppm) | | % DC | % DC | % DC | % DC |
| Compound I | Fluxapyroxad | Obs | Exp | Obs | Exp |
| 6.25 | 0 | 93 | — | 98 | — |
| 1.56 | 0 | 2 | — | 12 | — |
| 0.39 | 0 | 0 | — | 0 | — |
| 0.1 | 0 | 0 | — | 2 | — |
| 0 | 6.25 | 94 | — | 100 | — |
| 0 | 1.56 | 0 | — | 86 | — |
| 0 | 0.39 | 0 | — | 0 | — |
| 0 | 0.1 | 0 | — | 0 | — |
| 1.56 | 1.56 | 26 | 2 | — | 87.7 |
| 1.56 | 0.39 | 9 | 2 | 48 | 12 |
| 1.56 | 0.1 | 12 | 2 | 52 | 12 |

% DC Obs = Percent disease control observed
% DC Exp = Percent disease control expected

What is claimed:

1. A synergistic fungicidal mixture comprising a fungicidally effective amount of a compound of Formula I and fluxapyroxad, wherein the weight ratio of the compound of Formula I to fluxapyroxad is from about 1:1 to about 16:1, and wherein the mixture exhibits synergistic fungicidal activity between the compound of Formula I and fluxapyroxad

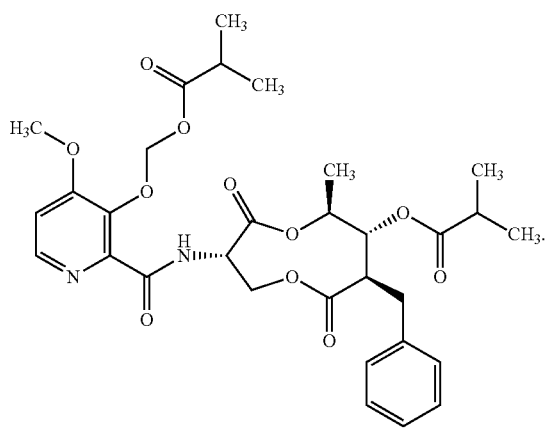

2. The mixture of claim 1, wherein the ratio of the compound of Formula I to fluxapyroxad is about 1 to about 1.

3. The mixture of claim 1, wherein the ratio of the compound of Formula I to fluxapyroxad is about 2 to about 1.

4. The mixture of claim 1, wherein the ratio of the compound of Formula I to fluxapyroxad is about 3 to about 1.

5. The mixture of claim 1, wherein the ratio of the compound of Formula I to fluxapyroxad is about 4 to about 1.

6. The mixture of claim 1, wherein the ratio of the compound of Formula I to fluxapyroxad is about 8 to about 1.

7. The mixture of claim 1, wherein the ratio of the compound of Formula I to fluxapyroxad is about 16 to about 1.

8. A fungicidal composition comprising a fungicidally effective amount of the fungicidal mixture of claim 1 and an agriculturally acceptable adjuvant or carrier.

9. A method of treating a plant, comprising the step of:
applying a fungicidally effective amount of a mixture that includes a compound of Formula I and fluxapyroxad, wherein the weight ratio of the compound of Formula I to fluxapyroxad is from about 1:1 to about 16:1 and wherein the mixture exhibits synergistic fungicidal activity between the compound of Formula I and fluxapyroxad, to a surface selected from at least one surface selected from the group of surfaces consisting of: at least one portion of a plant, soil adjacent to a plant, soil in contact with a plant, seeds, and equipment used in contact with a plant or a surface adjacent to a plant

I

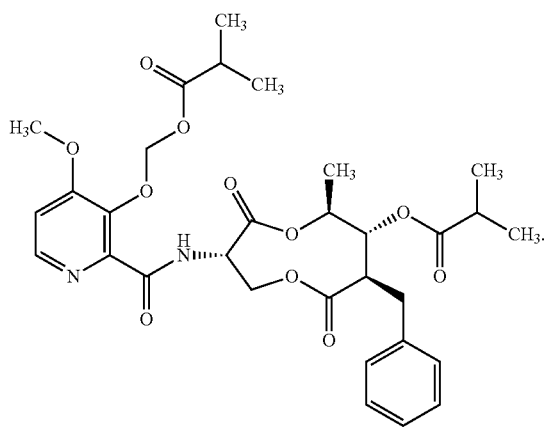

10. The method according to claim 9, wherein the fungicidally effective amount of the mixture is applied in the range of about 30 g/ha to about 200 g/ha of fluxapyroxad and about 35 g/ha to about 300 g/ha of the compound of Formula I.

11. The mixture of claim 1, wherein the mixture provides an observed level of fungicidal activity that is at least four times greater than the fungicidal activity expected from the individual fungicidal activity of the compound of Formula I and fluxapyroxad by the Colby equation.

12. The mixture of claim 1, wherein the ratio of the compound of Formula I to fluxapyroxad is from about 1:1 to about 8:1.

13. The mixture of claim 1, wherein the ratio of the compound of Formula I to fluxapyroxad is from about 1:1 to about 4:1.

14. The mixture of claim 1, wherein the ratio of the compound of Formula I to fluxapyroxad is from about 1:1 to about 2:1.

* * * * *